(12) United States Patent
Asakawa et al.

(10) Patent No.: US 9,687,824 B2
(45) Date of Patent: Jun. 27, 2017

(54) HETEROGENEOUS CATALYST AND CATALYST SYSTEM FOR PRODUCING 1,2-DICHLOROETHANE

(71) Applicant: TOSOH CORPORATION, Shunan-shi, Yamaguchi (JP)

(72) Inventors: Tetsuo Asakawa, Mie (JP); Sae Someya, Mie (JP); Tomokazu Ohashi, Mie (JP); Shinya Imatomi, Mie (JP); Hideyuki Hamaji, Mie (JP); Yoshihiko Mori, Mie (JP); Motohiro Oguri, Mie (JP)

(73) Assignee: TOSOH CORPORATION, Shunan (JP)

( * ) Notice: Subject to any disclaimer, the term of this patent is extended or adjusted under 35 U.S.C. 154(b) by 0 days.

(21) Appl. No.: 14/905,517

(22) PCT Filed: Jul. 17, 2014

(86) PCT No.: PCT/JP2014/069004
§ 371 (c)(1),
(2) Date: Jan. 15, 2016

(87) PCT Pub. No.: WO2015/008819
PCT Pub. Date: Jan. 22, 2015

(65) Prior Publication Data
US 2016/0167026 A1    Jun. 16, 2016

(30) Foreign Application Priority Data

Jul. 17, 2013  (JP) ................................. 2013-148891
Feb. 24, 2014  (JP) ................................. 2014-032919

(51) Int. Cl.
*B01J 27/138*    (2006.01)
*B01J 27/122*    (2006.01)
(Continued)

(52) U.S. Cl.
CPC .......... *B01J 27/138* (2013.01); *B01J 27/122* (2013.01); *B01J 35/02* (2013.01); *B01J 35/023* (2013.01);
(Continued)

(58) Field of Classification Search
None
See application file for complete search history.

(56) References Cited

U.S. PATENT DOCUMENTS 5,366,617 A * 11/1994 Bradley ................... B01J 29/61
                                                          208/137
5,817,594 A * 10/1998 McNamara ............. B01J 21/04
                                                        208/216 PP (Continued)

FOREIGN PATENT DOCUMENTS

DE   10 2005 023 955    11/2006
EP        0 775 522       5/1997

(Continued)

OTHER PUBLICATIONS

Mohamed, Effect of ceria-doped titania on the structure and acidic properties of MoO3/TiO2 catalysts, 2004, applied catalysis A: General, 267, pp. 135-142.*

(Continued)

*Primary Examiner* — Melvin C Mayes
*Assistant Examiner* — Stefanie Cohen
(74) *Attorney, Agent, or Firm* — Nixon & Vanderhye P.C.

(57) ABSTRACT

To provide a heterogeneous catalyst that exhibits high activity and high selectivity, specifically a catalyst suitable for oxychlorination to produce 1,2-dichloroethane from ethylene, and a catalyst system. Provided are: a heterogeneous catalyst supported on a porous carrier, characterized in that the integral value of the hysteresis occurring between an adsorption isotherm and a desorption isotherm by a gas (Continued)

adsorption method, is at most 19% to the total integral value of the adsorption isotherm; and a catalyst system for producing 1,2-dichloroethane, which comprises this catalyst and a diluent having a spherical shape, circular cylindrical shape or hollow cylindrical shape.

18 Claims, 1 Drawing Sheet

(51) Int. Cl.
*C07C 17/156* (2006.01)
*B01J 35/02* (2006.01)
*B01J 37/02* (2006.01)
*B01J 35/08* (2006.01)
*B01J 35/10* (2006.01)
B01J 35/00 (2006.01)
B01J 35/04 (2006.01)

(52) U.S. Cl.
CPC ............. *B01J 35/026* (2013.01); *B01J 35/08* (2013.01); *B01J 35/10* (2013.01); *B01J 35/109* (2013.01); *B01J 35/1061* (2013.01); *B01J 37/0207* (2013.01); *C07C 17/156* (2013.01); *B01J 35/002* (2013.01); *B01J 35/04* (2013.01); *B01J 35/108* (2013.01); *B01J 35/1085* (2013.01); *B01J 2208/00513* (2013.01); *B01J 2523/00* (2013.01)

(56) References Cited

U.S. PATENT DOCUMENTS

2009/0054225 A1* 2/2009 Mironov ................ B01J 23/002
502/167
2009/0114566 A1* 5/2009 Chen ....................... C10G 45/04
208/112

FOREIGN PATENT DOCUMENTS

| JP | 56-141842 | 11/1981 |
|---|---|---|
| JP | 57-136928 | 8/1982 |
| JP | 2000-254507 | 9/2000 |
| JP | 2006-110419 | 4/2006 |
| JP | 2007-508134 | 4/2007 |
| JP | 2010-051836 | 3/2010 |
| JP | 2012-187569 | 10/2012 |
| JP | 2012-532089 | 12/2012 |
| WO | WO 2010/076249 | 7/2010 |
| WO | WO 2012/084276 | 6/2012 |

OTHER PUBLICATIONS

Tchenar et al, RuO2 supported on V2O5—Al2O3 material as heterogeneous catalyst for cyclohexane oxidation reaction, 2012, Bull. Mater. Sci, vol. 35, No. 4, pp. 673-681.*
International Search Report for PCT/JP2014/069004, mailed Sep. 9, 2014, 2 pages.
International Preliminary Report on Patentability and Written Opinion mailed Jan. 19, 2016.
Extended European Search Resort issued in App. No. 14826546.5 dated Feb. 14, 2017.

* cited by examiner

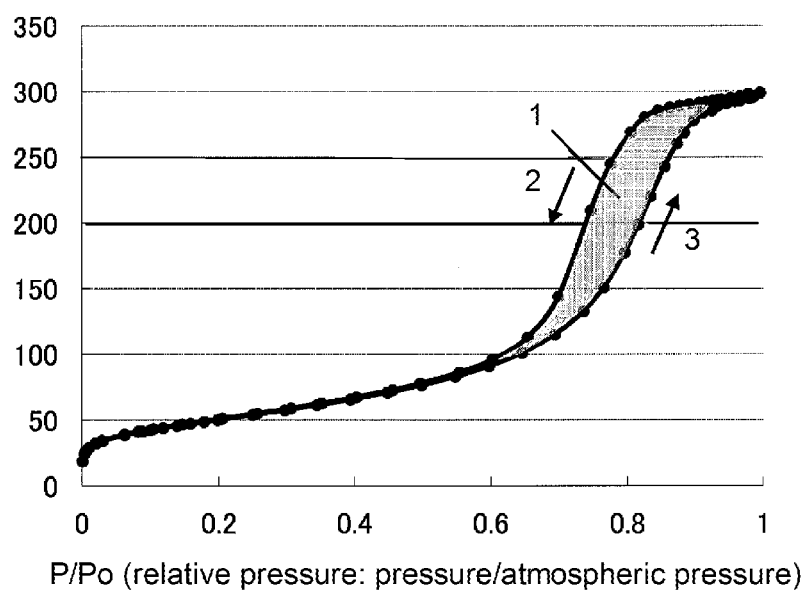

HETEROGENEOUS CATALYST AND CATALYST SYSTEM FOR PRODUCING 1,2-DICHLOROETHANE

This application is the U.S. national phase of International Application No. PCT/JP2014/069004 filed 17 Jul. 2014, which designated the U.S. and claims priority to JP Patent Application Nos. 2013-148891 filed 17 Jul. 2013, and 2014-032919 filed 24 Feb. 2014, the entire contents of each of which are hereby incorporated by reference.

TECHNICAL FIELD

The present invention relates to a novel heterogeneous catalyst, more particularly to a catalyst to be used for the production of petrochemical products or organic chemical products, specifically to a novel oxychlorination catalyst to produce 1,2-dichloroethane useful as a raw material for a vinyl chloride monomer, highly actively and highly selectively from ethylene; and to a method for producing 1,2-dichloroethane.

BACKGROUND ART

A heterogeneous catalyst can easily be separated from a gas phase or liquid phase reaction fluid, and it can be constantly held in a reactor to exhibit its function as a catalyst, and therefore, it is used in many petrochemical processes and processes for producing organic chemical products.

A supported copper chloride catalyst is used for the production of 1,2-dichloroethane (hereinafter abbreviated as EDC) by oxychlorination using ethylene, hydrogen chloride and oxygen as raw materials, which is one of typical very large petrochemical processes. Enlargement of an EDC production facility is progressing, and a large facility of 100,000 tons/year scale is running. In the production, the ethylene conversion and the selectivity for EDC are important factors, and even a difference at a level of 0.1% in them results in a large difference economically.

As a method for producing EDC by an oxychlorination reaction using ethylene, hydrogen chloride and oxygen as raw materials, a method of using a hollow cylindrical oxychlorination catalyst having copper chloride and potassium chloride supported on an alumina carrier, is known, and, for example, an oxychlorination catalyst having the cylindrical geometry defined, has been proposed (see e.g. Patent Document 1).

Further, this reaction system is an exothermic reaction, and therefore, at a site where the raw material concentration is high, like a reaction bed inlet, the reaction rate becomes high, and the heat generation becomes large. If the catalyst layer becomes a high temperature by the heat generation, and a hot spot is formed, there will be a problem such that due to a combustion reaction as a side reaction, increase of by-products or rapid catalyst deterioration is likely to proceed. Therefore, usually, formation of a hot spot in the fixed bed is reduced or eliminated by mixing the oxychlorination catalyst with a diluent (see e.g. Patent Documents 2 to 4).

PRIOR ART DOCUMENTS

Patent Documents

Patent Document 1: JP-A-56-141842
Patent Document 2: JP-A-57-136928
Patent Document 3: JP-A-2007-508134
Patent Document 4: JP-A-2000-254507

DISCLOSURE OF INVENTION

Technical Problem

As EDC production facilities, an air method process (ethylene, HCl and air are the main raw materials), an oxygen-enriched method process (using ethylene, HCl and air as the main raw materials, a small amount of oxygen is added) and an oxygen method process (ethylene, HCl and oxygen are the main raw materials) are known. In the air method and oxygen-enriched method processes, there is a room for improving a problem of unconverted ethylene, and in the oxygen method process, there is a problem in improving the productivity by a high activity catalyst, but the oxychlorination catalyst proposed by Patent Document 1 is still not yet satisfactory in its catalytic activity and EDC selectivity, and a catalyst to significantly improve the catalytic activity and EDC selectivity is still desired.

Further, also with respect to the diluent to be used for preventing a hot spot, in the case of a diluent with an irregular shape, obtained by mechanical pulverization, or one having a significantly smaller size than the diameter or length of the catalyst, there is a problem such that the pressure loss is thereby increased. Problems caused by such an increase of the pressure loss, such as a decrease in productivity due to the pressure loss, and requirement for a high pressure reaction equipment, are economically disadvantageous. Although it may be possible to prevent the pressure loss by using a diluent with a large diameter or length, the heat removal effect is thereby reduced so that no satisfactory heat removal effect is thereby obtainable. Therefore, the material, shape and size of the diluent to be selected, must be optimized in consideration of the balance between the heat removal effect and the pressure loss.

Solution to Problems

The present invention has been made in view of the above problems, and an object of the present invention is to provide a heterogeneous catalyst which exhibits high catalytic activity and EDC selectivity, in particular an oxychlorination catalyst.

As a result of intensive investigations to solve the above problems, the present inventors have found that a catalyst having a specific pore shape defined by a gas adsorption method, exhibits a high activity and a high selectivity, and, particularly in the oxychlorination, it exhibits a high activity and a high EDC selectivity, and have found a catalyst system for the production of EDC, characterized by comprising such a catalyst and a diluent selected from a spherical, cylindrical or hollow cylindrical shape, and a production method using such a catalyst system, and thus, they have accomplished the present invention.

That is, the present invention resides in the following [1] to [20].

[1] A catalyst which is a heterogeneous catalyst having a metal compound supported on a porous carrier and which is characterized in that the integral value of the hysteresis occurring between an adsorption isotherm and a desorption isotherm by a gas adsorption method, is at most 19% to the total integral value of the adsorption isotherm.

[2] The catalyst according to the above [1], wherein the porous carrier is alumina, silica, silica-alumina, zeolite, titanium oxide, zirconium oxide or magnesium oxide.

[3] The catalyst according to the above [1] or [2], wherein the metal in the metal compound is a metal in Group 1, Group 2 or Group 11 in the Periodic Table.
[4] The catalyst according to any one of the above [1] to [3], wherein the metal compound is an oxide or halide.
[5] The catalyst according to any one of the above [1] to [4], wherein the metal compound is copper chloride.
[6] The catalyst according to any one of the above [1] to [5], wherein the metal compound is copper chloride, and at least one metal chloride selected from the group consisting of potassium chloride, cesium chloride, sodium chloride and magnesium chloride.
[7] The catalyst according to the above [5] or [6], wherein the amount of copper chloride supported, is from 3 to 25 wt %.
[8] The catalyst according to the above [6] or [7], wherein the amount of the metal chloride supported, is from 0.1 to 20 wt %.
[9] The catalyst according to any one of the above [1] to [8], wherein the gas adsorption method is a nitrogen adsorption method.
[10] The catalyst according to any one of the above [1] to [9], wherein the heterogeneous catalyst has a hollow cylindrical shape.
[11] The catalyst according to the above [10], wherein the hollow cylindrical shape has an outer diameter of from 3 to 6 mm, an inner diameter of from 1 to less than 3 mm and a length of from 3 to 6 mm.
[12] The catalyst according to any one of the above [1] to [11], wherein the catalyst is used in an application for oxychlorination of ethylene.
[13] A method for producing 1,2-dichloroethane, which comprises carrying out oxychlorination of ethylene, hydrogen chloride and oxygen in the presence of the catalyst as defined in any one of the above [1] to [12].
[14] A catalyst system for producing 1,2-dichloroethane from ethylene, hydrogen chloride and oxygen, which comprises the catalyst as defined in any one of the above [1] to [12], and a diluent having a spherical shape, cylindrical shape or hollow cylindrical shape.
[15] The catalyst system for producing 1,2-dichloroethane according to the above [14], wherein the diluent is at least one member selected from the group consisting of, alumina, silica, alumina-silica, silicon carbide, aluminum nitride, carbon and graphite.
[16] The catalyst system for producing 1,2-dichloroethane according to the above [14] or [15], wherein the outer diameter D of the diluent having a spherical shape is a dimension (mm) of the following formula (1):

$$4.5 \leq D \leq 7.0 \tag{1}$$

[17] The catalyst system for producing 1,2-dichloroethane according to the above [14] or [15], wherein the outer diameter $De^1$ of the cylinder of the diluent having a cylindrical shape is a dimension (mm) of the following formula (2), and the length $L^1$ of the side surface thereof is a dimension (mm) of the following formula (3):

$$4.5 \leq De^1 \leq 7.0 \tag{2}$$

$$4.0 \leq L^1 \leq 7.0 \tag{3}$$

[18] The catalyst system for producing 1,2-dichloroethane according to the above [14] or [15], wherein the outer diameter $De^2$ of the hollow cylinder of the diluent having a hollow cylindrical shape is a dimension (mm) of the following formula (4), and the inner diameter Di thereof is a dimension (mm) of the following formula (5), the length $L^2$ of the side surface thereof is a dimension (mm) of the following formula (6), and the relation between the outer diameter $De^2$ and the inner diameter Di is represented by the formula (7):

$$4.5 \leq De^2 \leq 7.0 \tag{4}$$

$$1.5 \leq Di \leq 4.0 \tag{5}$$

$$4.0 \leq L^2 \leq 7.0 \tag{6}$$

$$De^2/3 \leq Di \tag{7}$$

[19] The catalyst system for producing 1,2-dichloroethane according to any one of the above [14] to [18], wherein the outer diameter of the diluent is a length equal to the length of the oxychlorination catalyst.
[20] A method for producing 1,2-dichloroethane, which is characterized by reacting ethylene, hydrogen chloride and oxygen in the presence of the catalyst system for producing 1,2-dichloroethane as defined in any one of the above [14] to [19].

Advantageous Effects of Invention

The novel heterogeneous catalyst and catalyst system of the present invention exhibit high ethylene conversion and EDC selectivity particularly when used for oxychlorination of ethylene, and thus are industrially very useful as means for producing EDC useful as a raw material for a vinyl chloride monomer, with high productivity.

BRIEF DESCRIPTION OF DRAWING

FIG. 1 is a graph showing an adsorption isotherm of nitrogen at the liquid nitrogen temperature. Hysteresis ratio= (desorption side adsorption isotherm area−adsorption side adsorption isotherm area)/(adsorption side adsorption isotherm area).

DESCRIPTION OF EMBODIMENTS

Now, the present invention will be described in detail.
The catalyst of the present invention is a heterogeneous catalyst having a metal compound supported on a porous carrier, and is one wherein the integral value of the hysteresis occurring between an adsorption isotherm and a desorption isotherm by a gas adsorption method, is at most 19% to the total integral value of the adsorption isotherm.
Here, the gas adsorption method is one defined in Shimadzu Critic Vol. 48, No. 1 (1991.6.) and is a method wherein gas molecules having a known adsorption occupying area are adsorbed on the surface of catalyst particles, and from the condensation of the gas molecules, the specific surface area and pore distribution are measured. As the gas molecules, nitrogen, argon or the like may be mentioned, and among them, nitrogen is preferred.
The adsorption isotherm is one obtained by plotting the relative pressure along the abscissa, and the number of adsorbed gas molecules or the volume of gas in the standard state along the ordinate, and one having the relative pressure changed from a low place to a high place is called an adsorption isotherm, and the reverse is called a desorption isotherm. Hysteresis is believed to occur by capillary condensation caused by the pore shape (cylindrical, conical, slit-shaped, ink bottle-shaped, etc.), and it refers to a mismatch in the adsorption isotherm between the adsorption side and the desorption side (see FIG. 1).

In the present invention, the integral value of the hysteresis is defined as the difference between the integral value of an adsorption isotherm and the integral value of a desorption isotherm in a relative pressure range under the measurement conditions.

Of the catalyst of the present invention, the integral value of the hysteresis occurring between an adsorption isotherm and a desorption isotherm by a gas adsorption method is at most 19% to the total integral value of the adsorption isotherm. It is considered that when it becomes at most 19%, the pore shape of the catalyst will change, so that pores of an ink bottle shape will decrease, and pores of a straight shape will increase. By such a shape change, the effect to improve the catalytic activity and selectivity is developed. Further, since it is possible to obtain a still higher activity, the integral value of the hysteresis occurring between the adsorption isotherm and the desorption isotherm by the gas adsorption method, is preferably at most 17.5% to the total integral value of the adsorption isotherm.

By the catalyst of the present invention, it becomes possible to continue the operation over a long period of time without impairing the activity and selectivity, and it can be used for an oxidation reaction, a reduction reaction, a hydrogenation reaction, a dehydrogenation reaction, an alkylation reaction, etc., but a high effect is expected particularly in the method for producing EDC from ethylene, hydrogen chloride and oxygen. Particularly, the effect to improve the catalytic activity is remarkable, and the activity of the catalyst according to the invention can be improved by 10% or more, whereby it is possible to use it as a catalyst for an oxygen method process wherein high productivity is required, and also to utilize it for improving the conversion of unconverted ethylene in air method and oxygen-enriched method processes. In the catalyst of the present invention, the shape of the pore distribution is not particularly limited, and for example, a monomodal pore distribution, a bimodal pore distribution or the like, may be mentioned. Among them, the bimodal pore shape is preferred, since the catalytic activity and selectivity will be thereby improved. The pore diameter of bimodal pores is not particularly limited, but, a bimodal type having pores with pore diameters in the range of from 3 to less than 15 nm and pores with pore diameters in a range of from 15 to 50 nm, is preferred, whereby it becomes possible to further improve the activity and selectivity.

The catalyst of the present invention is a heterogeneous catalyst having a metal compound supported on a porous carrier, and is preferably granules. The porous carrier is not particularly limited, and may, for example, be alumina, silica, silica-alumina, zeolite, titanium oxide, zirconium oxide or magnesium oxide. Among them, alumina is preferred, since it has high affinity with a metal compound as a catalyst active component, and particularly preferred is a porous alumina carrier having pores. Here, in the porous alumina carrier, silicon or iron derived from the alumina raw material, carbon such as a releasing agent, or an additive such as silica or titanium may be mixed as long as it is not adversely influential over the catalytic reaction. Such an alumina carrier may be molded by any method and may, for example, be molded by extrusion molding or compression molding. There is no particular limitations to the size of the hollow cylindrical shape, and in particular, since the catalyst will be excellent in catalytic activity, a cylindrical shape having an outer diameter of the hollow cylinder of from 3 to 6 mm, an inner diameter of from 1 to less than 3 mm, and a length of the side surface of from 3 to 6 mm, is preferred, and further, a cylindrical shape having an outside diameter of from 5 to 6 mm, an inner diameter of from 2 to less than 3 mm, and a length of from 4 to 6 mm, is more preferred.

The metal in the metal compound supported on the porous carrier is not particularly limited, but a metal in Group 1, Group 2 or Group 11 of the Periodic Table is preferred. The metal compound is not particularly limited and may be an oxide or halide, and a metal chloride is preferred. As the metal oxide, lithium oxide, sodium oxide, potassium oxide, rubidium oxide, cesium oxide, magnesium oxide, calcium oxide, strontium oxide, barium oxide, copper oxide, silver oxide or the like, may mentioned. As the halide, lithium chloride, sodium chloride, potassium chloride, rubidium chloride, magnesium chloride, calcium chloride, strontium chloride, barium chloride, copper chloride, silver chloride or the like, may be mentioned. Among them, copper chloride is preferred, since it exhibits a particularly high activity in the oxychlorination. Here, as the copper chloride, cuprous and/or cupric chloride may be mentioned, and among them, cupric chloride is preferred, since it will be an oxychlorination catalyst which is excellent particularly in stability.

The supported amount of the metal compound is not particularly limited so long as the oxychlorination catalyst acts as a catalyst, and is preferably from 1 to 30 wt %, more preferably from 2 to 28 wt %, since it is thereby possible to obtain an oxychlorination catalyst which is excellent in catalytic activity.

In a case where the metal compound is copper chloride, the supported amount of copper chloride is preferably from 3 to 25 wt %, more preferably from 8 to 20 wt %, since it is thereby possible to obtain an oxychlorination catalyst which is excellent in catalytic activity.

Further, as the metal compound, in addition to copper chloride, other metal chlorides are preferably supported. Such other metal chlorides are not particularly limited, and may, for example, be lithium chloride, sodium chloride, potassium chloride, rubidium chloride, cesium chloride, magnesium chloride, calcium chloride, strontium chloride, etc., and among them, potassium chloride, cesium chloride, sodium chloride and magnesium chloride are preferred, since the stability of the oxychlorination catalyst is thereby increased. The supported amount of the metal chlorides is not particularly limited so long as the oxychlorination catalyst acts as a catalyst, and is preferably from 0.1 to 20 wt %, more preferably from 0.1 to 10 wt %, since it contributes to stability of copper chloride and it is thereby possible to obtain an oxychlorination catalyst having excellent catalytic activity. Also, the supported ratio of other metal chlorides to copper chloride in the oxychlorination catalyst of the present invention is not particularly limited so long as the oxychlorination catalyst acts as a catalyst, but particularly, the ratio of other metal chlorides is preferably from 0.1 to 3 mol, more preferably from 0.1 to 1.3 mol, per 1 mol of copper chloride, since it is thereby possible to obtain an oxychlorination catalyst excellent in catalytic activity and stability.

The oxychlorination catalyst of the present invention may be in any shape, but, for example, a spherical, honeycomb or hollow cylindrical shape may be mentioned. Among them, a hollow cylindrical shape is preferred from the viewpoint of excellent fracture strength. Its geometry in not particularly limited, and it is preferably a cylindrical shape having an outer diameter of from 2 to 8 mm, an inner diameter of from 1 to 7 mm and a length of from 2 to 8 mm, more preferably an outer diameter of from 3 to 6 mm, an inner diameter of from 1 to less than 3 mm and a length of from 3 to 6 mm, since the catalyst will thereby be excellent in catalytic activity.

The catalyst of the present invention may be produced by any method, and, for example, a method of production by supporting a metal compound on a porous carrier, may be mentioned. As the supporting method in such a case, for example, a dipping method, an impregnation method, a coprecipitation method or the like, may be mentioned, and among them, a dipping method is preferred, since the operation is simple, and it is excellent in productivity.

Here, the dipping method is a method wherein a porous carrier is immersed in a solution (immersion solution) containing a metal compound, after the immersion treatment, the porous carrier and the solution are separated, and the porous carrier having the metal compound deposited thereon, is dried, followed by firing treatment to obtain a catalyst.

In a case where as the immersion solution in the dipping method, an aqueous solution of copper chloride and at least one metal chloride selected from the group consisting of potassium chloride, cesium chloride, sodium chloride and magnesium chloride, is to be used, the concentration of copper chloride in the aqueous solution is not particularly limited, but is preferably from 50 to 300 g/L, more preferably from 70 to 270 g/L, since the catalytic activity is high. The concentration of potassium chloride in the aqueous solution is not particularly limited, but is preferably from 10 to 280 g/L, more preferably from 20 to 260 g/L, since the catalytic activity is high. The concentration of cesium chloride in the aqueous solution is not particularly limited, but is preferably from 30 to 180 g/L, more preferably from 50 to 150 g/L, since the catalytic activity is high. The concentration of sodium chloride in the aqueous solution is not particularly limited, but is preferably from 10 to 130 g/L, more preferably from 20 to 100 g/L, since the catalytic activity is high. The concentration of magnesium chloride in the aqueous solution is not particularly limited, but is preferably from 50 to 220 g/L, more preferably from 80 to 200 g/L, since the catalytic activity is high.

The temperature during the immersion is not particularly limited, and may, for example, be from 0 to 80° C., preferably from 10 to 50° C. The reaction pressure is not particularly limited, but is usually atmospheric pressure. Further, the immersion time depends on the temperature or the concentration of the immersion solution, and cannot generally be defined, but is usually from 1 to 10 hours. There is no particular limitation to the atmosphere during the reaction, but an atmosphere substituted by an inert gas such as nitrogen, argon or helium, may be used.

In the production of an oxychlorination catalyst by the dipping method, the order of supporting the metal compounds is not particularly limited, and they may be supported all at once or may be supported dividedly. Metal compounds may be supported in a state of the respective aqueous solutions, if necessary.

The drying temperature is not particularly limited, but is preferably from 0 to 250° C., more preferably from 30 to 200° C. The drying time is not particularly limited, but is preferably from 1 to 20 hours, more preferably from 2 to 10 hours. The atmosphere during the drying is not particularly limited, but the drying is usually carried out in air. Otherwise, the drying may be conducted in an atmosphere substituted by an inert gas such as nitrogen, argon or helium.

Although the firing temperature is not particularly limited, it is preferably from 0 to 500° C., more preferably from 100 to 400° C. Although the firing time is not particularly limited, it is preferably from 1 to 20 hours, more preferably from 2 to 10 hours. Further, the firing may be conducted in an atmosphere substituted by an inert gas such as nitrogen, argon or helium.

The integral value of the hysteresis occurring between an adsorption isotherm and a desorption isotherm by a gas adsorption method, of the catalyst of the present invention, can be controlled by treatment of the carrier with hydrochloric acid and by subsequent high-temperature firing. The amount of hydrochloric acid is not particularly limited, but is preferably from 10 to 1,000 ml, more preferably from 20 to 200 ml, per 50 g of the carrier. The immersion time is not particularly limited, but is preferably from 1 to 20 hours, more preferably from 2 to 10 hours. The temperature at the time of immersion is not particularly limited, but may, for example, be from 0 to 80° C., preferably from 10 to 50° C.

In the present invention, it is possible to produce EDC by carrying out the oxychlorination reaction in the presence of the above-described oxychlorination catalyst, using ethylene, hydrogen chloride and oxygen as the raw materials.

In the present invention, the reaction system for producing EDC by the oxychlorination reaction using ethylene, hydrogen chloride and oxygen as the raw materials, is not particularly limited, and it is possible to carry out the reaction in any optional reaction system, for example, in a fixed bed flow system or in a fluidized bed flow system. Among them, it is preferably carried out in a fixed bed flow system, since the apparatus is thereby simple. The reaction temperature is not particularly limited, but is preferably from 100° C. to 400° C., more preferably from 150° C. to 350° C., since conversion to EDC can thereby be efficiently carried out. The reaction pressure is not particularly limited, but may usually be from 0.01 to 2 MPa, preferably from 0.05 to 1 MPa by absolute pressure. Further, the gas hourly space velocity (GHSV) during the fixed-bed flow reaction is preferably from $10\ hr^{-1}$ to $10,000\ hr^{-1}$, more preferably from $30\ hr^{-1}$ to $8,000\ hr^{-1}$, since conversion to EDC can thereby be efficiently carried out. Here, the gas hourly space velocity (GHSV) represents the amount of ethylene supplied in unit time (hr) per unit volume of the catalyst.

Here, ethylene, hydrogen chloride and oxygen, may be used as they are, or they may be used as diluted with an inert gas. The insert gas is not particularly limited, but may, for example, be nitrogen, helium or argon, and such inert gases may be used not only alone, but also as a mixture of two or more of them. As typical examples, a so-called air method using air for oxygen as one of the raw materials, an oxygen-enriched method using air by adding oxygen thereto, and an oxygen method which does not use an inert gas such as nitrogen, are widely adopted and practically used as industrial processes. The oxychlorination catalyst of the present invention can be suitably used in any process.

The material for the reaction column is not particularly limited, and may, for example, be nickel, a nickel alloy, stainless steel or the like. Among them, nickel and a nickel alloy are preferred, since they are excellent in corrosion resistance to hydrogen chloride.

Since the oxychlorination reaction is an exothermic reaction, a diluent may be mixed to the catalyst layer as the case requires, to constitute a catalyst system for producing EDC which comprises the oxychlorination catalyst and the diluent. The shape of the diluent is not particularly limited and may, for example, be spherical, cylindrical, hollow cylindrical, or the like, but a diluent having a spherical, cylindrical or hollow cylindrical shape is preferred, since it is thereby possible to attain a good heat removal effect and low pressure loss. In the case of a spherical shape, the following size (mm) is preferred wherein D is the diameter:

$$4.5 \leq D \leq 7.0 \quad (1)$$

In the case of a cylindrical shape, the following dimensions (mm) are preferred wherein $De^1$ is the diameter, and $L^1$ is the length of the side surface:

$$4.5 \leq De^1 \leq 7.0 \quad (2)$$

$$4.0 \leq L^1 \leq 7.0 \quad (3)$$

In the case of a hollow cylindrical shape, constituted by one cylinder having a cylindrical through-hole with a smaller diameter formed in parallel with the side surface of the cylinder, the following dimensions (mm) are preferred wherein $De^2$ is the outer diameter of the hollow cylinder of the diluent, Di is the inner diameter thereof, and $L^2$ is the length of the side surface thereof, including the relation between the outer diameter $De^2$ and the inner diameter Di:

$$4.5 \leq De^2 \leq 7.0 \quad (4)$$

$$1.5 \leq Di \leq 4.0 \quad (5)$$

$$4.0 \leq L^2 \leq 7.0 \quad (6)$$

$$De^2/3 \leq Di \quad (7)$$

Among them, the hollow cylindrical shape is preferred, since it is thereby possible to reduce the pressure loss. If the size is large, the pressure loss may be small, but the heat removal effect tends to decrease, such being disadvantageous. On the other hand, if the size is small, although the heat removal effect may be large, the pressure loss tends to be large, such being disadvantageous.

In order to obtain a good heat removal effect, the material for the diluent is preferably at least one member selected from the group consisting of alumina, silica, alumina-silica, silicon carbide, aluminum nitride and graphite. So that these diluents do not adversely affect the oxychlorination reaction, with respect to alumina, silica, alumina-silica, silicon carbide and aluminum nitride, a sintered body having a specific surface area of at most 5 $m^2/g$ is preferred, and with respect to graphite, a sintered body of at most 20 $m^2/g$ is preferred. By a diluent using such a sintered body as its material, mechanical wear is suppressed in the course of producing EDC, which is likely to occur in a porous molded product, and it is possible to produce EDC stably without increasing the pressure loss.

In the present invention, the mixing ratio of the oxychlorination catalyst and the diluent may be modified within a range of from 5:95 to 95:5 in consideration of the amount of heat generation. Further, a large amount of the diluent may be used at a site where the raw material concentration is high, like the reaction bed inlet, while a small amount of the diluent may be used at the outlet side, or the oxychlorination catalyst may be used alone throughout the process.

EXAMPLES

Now, Examples of the present invention will be described, but it should be understood that the present invention is by no means limited to these Examples.

The measurement methods and reaction evaluation methods used in Examples are as follows.
<Measurement of Hysteresis>

The measurement of the hysteresis was carried out by using a nitrogen adsorption method specific surface area•pore distribution measuring apparatus (Micromeritics Japan, trade name: ASAP2400) under conditions of the liquid nitrogen temperature and a nitrogen relative pressure of from 0.001 to 0.995. For the integral value of the hysteresis, the integral value of an adsorption isotherm and the integral value of a desorption isotherm were, respectively, obtained in a range of relative pressure of from 0.001 to 0.995, and the integral value of the hysteresis is the difference obtained by subtracting the former from the latter.
<Quantitative Determination of Copper Chloride and Chlorides>

The quantitative determination of copper chloride and other chlorides was carried out by means of a scanning X-ray fluorescence analyzer (manufactured by Rigaku Corporation, (trade name) ZSX PrimusII), and by pulverizing about 3 g of the catalyst, then preparing a sample plate by a pressure press, and measuring this plate by using a Rh tube under the conditions of tube voltage/tube current being 50 kV/60 mA. The obtained Cu and K concentrations were, respectively, converted to $CuCl_2$ and KCl, and listed in Table 1.
<Reaction Method>

For the reaction evaluation of an oxychlorination catalyst, a fixed bed gas phase flow reaction apparatus using a glass reaction tube (inner diameter: 22 mm, length: 600 mm) was used. In the middle of the glass reaction tube, the oxychlorination catalyst was filled, and ethylene, hydrogen chloride, molecular oxygen and diluent nitrogen were supplied to the catalyst layer. In Examples 1 to 8 and 29 to 35 and Comparative Examples 1 to 4 and 15 to 16, the raw material composition was adjusted to be an air method composition (ethylene: 32 ml/min, hydrogen chloride: 64 ml/min, oxygen: 13 ml/min, nitrogen: 91 ml/min). In Examples 9 to 18 and Comparative Examples 5 to 9, it was adjusted to be an oxygen-enriched method composition (ethylene: 24 ml/min, hydrogen chloride: 44 ml/min, oxygen: 20 ml/min, nitrogen: 413 ml/min). In Examples 19 to 28 and Comparative Examples 10 to 14, it was adjusted to be an oxygen method composition (ethylene: 190 ml/min, hydrogen chloride: 30 ml/min, oxygen: 8 ml/min, nitrogen: 122 ml/min). For the specific activity, in Examples 1 to 8 and 29 to 35 and Comparative Examples 1 to 4 and 15 to 16, an ethylene conversion was obtained in each of a case where 2 cm before the inlet to the catalyst layer was controlled to be 220° C. and a case where the top temperature of the catalyst layer was controlled to be 270° C., and the average value of the ethylene conversion to the filling rate was set to be the activity. In Examples 9 to 28 and Comparative Examples 5 to 14, the specific activity was obtained from the ethylene conversion in a case where 2 cm before the inlet to the catalyst layer was controlled to be 220° C. Further, the EDC selectivity was obtained by controlling 2 cm before the inlet to the catalyst layer to be 220° C. The outlet gas and the reaction liquid under each reaction condition were collected, and using a gas chromatograph, the gas components and the liquid components were analyzed separately. The gas components were analyzed by means of a gas chromatograph (manufactured by Shimadzu Corporation, trade name: GC-14A). As fillers, PorapakQ (trade name) manufactured by Waters and MS-5A (trade name) manufactured by GL Sciences Inc. were used. The liquid components were analyzed by means of a gas chromatograph (manufactured by Shimadzu Corporation, trade name: GC-1700). As a separation column, a capillary column (manufactured by GL Sciences Inc., trade name: TC-1) was used.

Example 1

50 g of a hollow cylindrical alumina carrier (trade name N611N3, outer diameter: 4.9 mm, inner diameter: 1.8 mm, length: 3.9 mm) manufactured by JGC C&C., was immersed in 100 ml of 1N hydrochloric acid for 2 hours, followed by draining, drying at 120° C. and firing at 500° C. for 5 hours in the air, to obtain a hollow cylindrical alumina carrier wherein the area ratio of the adsorption-desorption isotherm hysteresis in the gas adsorption method was 12.5% to the integral value of the adsorption isotherm. To 30 g of this alumina carrier, water was sufficiently absorbed, and then, it was immersed in 80 mL of an aqueous solution of $CuCl_2$=74 g/L and KCl=136 g/L for 4 hours. The alumina carrier was taken out from the immersion solution and dried at 120° C. for 2 hours using a muffle furnace. It was then fired at 250° C. for 4 hours, to prepare an oxychlorination catalyst wherein the K/Cu ratio was 0.80. The area ratio of the adsorption-desorption isotherm hysteresis in the gas adsorption method, was 13.6% to the integral value of the adsorption isotherm. Using this catalyst, the evaluation was carried out under the air method conditions, and as a result, the specific activity was 159, and the EDC selectivity was 99.6%. Here, the specific activity was evaluated by taking the activity of Comparative Example 2 as 100.

Example 2

An oxychlorination catalyst wherein the K/Cu ratio was 0.80, was prepared under the same conditions as in Example 1 except that it was immersed in 80 mL of an aqueous solution of $CuCl_2$=255 g/L and KCl=140 g/L for two hours. The area ratio of the adsorption-desorption isotherm hysteresis in the gas adsorption method, was 14.0% to the integral value of the adsorption isotherm. Using this catalyst, the evaluation was carried out under the air method conditions, and as a result, the specific activity was 142, and the EDC selectivity was 99.4%. Here, the specific activity was evaluated by taking Comparative Example 2 as 100.

Example 3

50 g of a hollow cylindrical alumina carrier (trade name N611N3, outer diameter: 4.9 mm, inner diameter: 1.8 mm, length: 3.9 mm) manufactured by JGC C&C., was immersed in 100 ml of 1N hydrochloric acid for 2 hours, followed by draining, drying at 120° C. and firing at 700° C. for 5 hours in the air, to obtain a hollow cylindrical alumina carrier wherein the area ratio of the adsorption-desorption isotherm hysteresis in the gas adsorption method was 14.4% to the integral value of the adsorption isotherm. To 30 g of this alumina carrier, water was sufficiently absorbed, and then, it was immersed in 80 mL of an aqueous solution of $CuCl_2$=174 g/L and KCl=136 g/L for 4 hours. The alumina carrier was taken out from the immersion solution and dried at 120° C. for 2 hours using a muffle furnace. Then, it was fired at 420° C. for 4 hours, to prepare an oxychlorination catalyst wherein the K/Cu ratio was 0.80. The area ratio of the adsorption-desorption isotherm hysteresis in the gas adsorption method, was 17.3% to the integral value of the adsorption isotherm. Using this catalyst, the evaluation was carried out under the air method conditions, and as a result, the specific activity was 134, and the EDC selectivity was 99.3%. Here, the specific activity was evaluated by taking Comparative Example 2 as 100.

Example 4

An oxychlorination catalyst wherein the K/Cu ratio was 0.80, was prepared under the same conditions as in Example 3, except that it was immersed in 80 mL of an aqueous solution of $CuCl_2$=255 g/L and KCl=140 g/L for 2 hours and fired at 300° C. for 4 hours. The area ratio of the adsorption-desorption isotherm hysteresis in the gas adsorption method, was 18.9% to the integral value of the adsorption isotherm. Using this catalyst, the evaluation was carried out under the air method conditions, and as a result, the specific activity was 120, and the EDC selectivity was 99.2%. Here, the specific activity was evaluated by taking Comparative Example 2 as 100.

Comparative Example 1

50 g of a hollow cylindrical alumina carrier (trade name N611N3, outer diameter: 4.9 mm, inner diameter: 1.8 mm, length: 3.9 mm) manufactured by JGC C&C., was immersed in pure water for 1 hour, followed by draining, drying at 120° C. and firing at 500° C. for 5 hours in the air, to obtain a hollow cylindrical alumina carrier wherein the area ratio of the adsorption-desorption isotherm hysteresis in the gas adsorption method was 15.2% to the integral value of the adsorption isotherm. To 30 g of this alumina carrier, water was sufficiently absorbed and then, it was immersed in 80 mL of an aqueous solution of $CuCl_2$=270 g/L and KCl=150 g/L for 30 minutes. The alumina carrier was taken out from the immersion solution and dried at 120° C. for 2 hours using a muffle furnace. Then, it was fired at 420° C. for 6 hours, to prepare an oxychlorination catalyst wherein the K/Cu ratio was 0.80. The area ratio of the adsorption-desorption isotherm hysteresis in the gas adsorption method, was 23.4% to the integral value of the adsorption isotherm. Using this catalyst, the evaluation was carried out under the air method conditions, and as a result, the specific activity was 107, and the EDC selectivity was 99.1%. Here, the specific activity was evaluated by taking Comparative Example 2 as 100.

Comparative Example 2

50 g of a hollow cylindrical alumina carrier (trade name N611N3, outer diameter: 4.9 mm, inner diameter: 1.8 mm, length: 3.9 mm) manufactured by JGC C&C., was immersed in pure water for 1 hour, followed by draining, drying at 120° C. and firing at 700° C. for 5 hours in the air, to obtain a hollow cylindrical alumina carrier wherein the area ratio of the adsorption-desorption isotherm hysteresis in the gas adsorption method was 16.2% to the integral value of the adsorption isotherm. To 30 g of this alumina carrier, water was fully absorbed, and then, it was immersed in 80 mL of an aqueous solution of $CuCl_2$=255 g/L and KCl=140 g/L for two hours. The alumina carrier was taken out from the immersion solution and dried at 120° C. for 2 hours using a muffle furnace. Then, it was fired at 420° C. for 6 hours, to prepare an oxychlorination catalyst wherein the K/Cu ratio was 0.80. The area ratio of the adsorption-desorption isotherm hysteresis in the gas adsorption method, was 24.5% to the integral value of the adsorption isotherm. Using this catalyst, the evaluation was carried out under the air method conditions, and as the result, the specific activity was 100, and the EDC selectivity was 98.9%. Here, the specific activity was evaluated by taking Comparative Example 2 as 100.

Example 5

An oxychlorination catalyst wherein the K/Cu ratio was 0.15, was prepared under the same conditions as in Example 1 except that the concentration of the immersion solution was changed to $CuCl_2$=207 g/L and KCl=22 g/L. The area ratio of the adsorption-desorption isotherm hysteresis in the gas adsorption method, was 13.1% to the integral value of the adsorption isotherm. Using this catalyst, the evaluation was carried out under the air method conditions, and as a result, the specific activity was 251, and the EDC selectivity was 99.3%. Here, the specific activity was evaluated by taking Comparative Example 2 as 100.

Example 6

An oxychlorination catalyst wherein the K/Cu ratio was 0.15, was prepared under the same conditions as in Example 2 except that the concentration of the immersion solution was changed to $CuCl_2$=250 g/L and KCl=30 g/L. The area ratio of the adsorption-desorption isotherm hysteresis in the gas adsorption method, was 13.6% to the integral value of the adsorption isotherm. Using this catalyst, the evaluation was carried out under the air method conditions, and as a result, the specific activity was 234, and the EDC selectivity was 99.1%. Here, the specific activity was evaluated by taking Comparative Example 2 as 100.

Example 7

An oxychlorination catalyst wherein the K/Cu ratio was 0.15, was prepared under the same conditions as in Example 3 except that the concentration of the immersion solution was changed to $CuCl_2$=207 g/L and KCl=22 g/L. The area ratio of the adsorption-desorption isotherm hysteresis in the gas adsorption method was 17.2% to the integral value of the adsorption isotherm. Using this catalyst, the evaluation was carried out under the air method conditions, and as a result, the specific activity was 226, and the EDC selectivity was 99.0%. Here, the specific activity was evaluated by taking Comparative Example 2 as 100.

Example 8

An oxychlorination catalyst wherein the K/Cu ratio was 0.15, was prepared under the same conditions as in Example 4 except that the concentration of the immersion solution was changed to $CuCl_2$=250 g/L and KCl=30 g/L. The area ratio of the adsorption-desorption isotherm hysteresis in the gas adsorption method was 18.4% to the integral value of the adsorption isotherm. Using this catalyst, the evaluation was carried out under the air method conditions, and as a result, the specific activity was 212, and the EDC selectivity was 98.8%. Here, the specific activity was evaluated by taking Comparative Example 2 as 100.

Comparative Example 3

An oxychlorination catalyst wherein the K/Cu ratio was 0.15, was prepared under the same conditions as in Comparative Example 1 except that it was immersed in 80 mL of an aqueous solution of $CuCl_2$=295 g/L and KCl=32 g/L for 1 hour. The area ratio of the adsorption-desorption isotherm hysteresis in the gas adsorption method was 23.9% to the integral value of the adsorption isotherm. Using this catalyst, the evaluation was carried out under the air method conditions, and as a result, the specific activity was 199, and the EDC selectivity was 98.6%. Here, the specific activity was evaluated by taking Comparative Example 2 as 100.

Comparative Example 4

An oxychlorination catalyst wherein the K/Cu ratio was 0.15, was prepared under the same conditions as in Comparative Example 2 except that the concentration of the immersion solution was changed to $CuCl_2$=250 g/L and KCl=30 g/L. The area ratio of the adsorption-desorption isotherm hysteresis in the gas adsorption method was 24.1% to the integral value of the adsorption isotherm. Using this catalyst, the evaluation was carried out under the air method conditions, and as a result, the specific activity was 192, and the EDC selectivity was 98.4%. Here, the specific activity was evaluated by taking Comparative Example 2 as 100.

TABLE 1

Evaluation results under air method conditions

| | Ex. 1 | Ex. 2 | Ex. 3 | Ex. 4 | Comp. Ex. 1 | Comp. Ex. 2 | Ex. 5 | Ex. 6 | Ex. 7 | Ex. 8 | Comp. Ex. 3 | Comp. Ex. 4 |
|---|---|---|---|---|---|---|---|---|---|---|---|---|
| Shape | | | Hollow cylindrical | | | | | | Hollow cylindrical | | | |
| Hysteresis ratio (%) | 13.6 | 14.0 | 17.3 | 18.9 | 23.4 | 24.5 | 13.1 | 13.6 | 17.2 | 18.4 | 23.9 | 24.1 |
| Supported amount $CuCl_2$ (wt %) | 13.1 | 13.4 | 12.7 | 12.7 | 11.2 | 12.5 | 13.3 | 13.4 | 14.2 | 12.8 | 13.6 | 12.5 |
| Supported amount KCl (wt %) | 5.8 | 5.9 | 5.6 | 5.6 | 4.9 | 5.5 | 1.1 | 1.1 | 1.2 | 1.1 | 1.1 | 1.0 |
| K/Cu ratio (mol/mol) | 0.08 | 0.80 | 0.80 | 0.80 | 0.80 | 0.80 | 0.15 | 0.15 | 0.15 | 0.15 | 0.15 | 0.15 |
| Specific activity | 159 | 142 | 134 | 120 | 107 | 100 | 251 | 234 | 226 | 212 | 199 | 192 |
| EDC selectivity (%) | 99.6 | 99.4 | 99.3 | 99.2 | 99.1 | 98.9 | 99.3 | 99.1 | 99.0 | 98.8 | 98.6 | 98.4 |

*Specific activity standard: Comparative Example 2

Example 9

An oxychlorination catalyst wherein the K/Cu ratio was 0.50, was prepared under the same conditions as in Example 1 except that the composition of the immersion solution was changed to $CuCl_2$=161 g/L and KCl=98 g/L. The area ratio of the adsorption-desorption isotherm hysteresis in the gas adsorption method, was 13.2% to the integral value of the adsorption isotherm. Using this catalyst, the evaluation was carried out under the oxygen enriched method conditions, and as a result, the specific activity was 119. Here, the specific activity was evaluated by taking Comparative Example 5 as 100.

Example 10

An oxychlorination catalyst wherein the Cs/Cu ratio was 0.50, was prepared under the same conditions as in Example 1 except that the composition of the immersion solution was changed to $CuCl_2=161$ g/L and CsCl=221 g/L. The area ratio of the adsorption-desorption isotherm hysteresis in the gas adsorption method, was 13.5% to the integral value of the adsorption isotherm. Using this catalyst, the evaluation was carried out under the oxygen enriched method conditions, and as a result, the specific activity was 118. Here, the specific activity was evaluated by taking Comparative Example 5 as 100.

Example 11

An oxychlorination catalyst wherein the Na/Cu ratio was 0.50, was prepared under the same conditions as in Example 1 except that the composition of the immersion solution was changed to $CuCl_2=161$ g/L and NaCl=77 g/L and it was fired at 400° C. for 2 hours. The area ratio of the adsorption-desorption isotherm hysteresis in the gas adsorption method, was 13.3% to the integral value of the adsorption isotherm. Using this catalyst, the evaluation was carried out under the oxygen enriched method conditions, and as a result, the specific activity was 177. Here, the specific activity was evaluated by taking Comparative Example 5 as 100.

Example 12

An oxychlorination catalyst wherein the Mg/Cu ratio was 0.50, was prepared under the same conditions as in Example 1 except that the composition of the immersion solution was changed to $CuCl_2=161$ g/L and $MgCl_2.2H_2O=267$ g/L, and it was fired at 400° C. for 2 hours. The area ratio of the adsorption-desorption isotherm hysteresis in the gas adsorption method, was 13.1% to the integral value of the adsorption isotherm. Using this catalyst, the evaluation was carried out under the oxygen enriched method conditions, and as a result, the specific activity was 260. Here, the specific activity was evaluated by taking Comparative Example 5 as 100.

Example 13

An oxychlorination catalyst wherein the (Na+Mg)/Cu ratio was 0.50, was prepared under the same conditions as in Example 1 except that the composition of the immersion solution was changed to $CuCl_2=161$ g/L, NaCl=26 g/L and $MgCl_2.2H_2O=180$ g/L, and it was fired at 400° C. for 2 hours. The area ratio of the adsorption-desorption isotherm hysteresis in the gas adsorption method, was 13.4% to the integral value of the adsorption isotherm. Using this catalyst, the evaluation was carried out under the oxygen enriched method conditions, and as a result, the specific activity was 198. Here, the specific activity was evaluated by taking Comparative Example 5 as 100.

Example 14

An oxychlorination catalyst wherein the K/Cu ratio was 0.50, was prepared under the same conditions as in Example 3 except that the composition of the immersion solution was changed to $CuCl_2=161$ g/L and KCl=98 g/L, and it was fired at 250° C. for 4 hours. The area ratio of the adsorption-desorption isotherm hysteresis in the gas adsorption method was 15.0% to the integral value of the adsorption isotherm. Using this catalyst, the evaluation was carried out under the oxygen enriched method conditions, and as a result, the specific activity was 117. Here, the specific activity was evaluated by taking Comparative Example 5 as 100.

Example 15

An oxychlorination catalyst wherein the Cs/Cu ratio was 0.50, was prepared under the same conditions as in Example 3 except that the composition of the immersion solution was changed to $CuCl_2=161$ g/L and CsCl=221 g/L, and it was fired at 250° C. for 4 hours. The area ratio of the adsorption-desorption isotherm hysteresis in the gas adsorption method, was 15.1% to the integral value of the adsorption isotherm. Using this catalyst, the evaluation was carried out under the oxygen enriched method conditions, and as a result, the specific activity was 115. Here, the specific activity was evaluated by taking Comparative Example 5 as 100.

Example 16

An oxychlorination catalyst wherein the Na/Cu ratio was 0.50, was prepared under the same conditions as in Example 3 except that the composition of the immersion solution was changed to $CuCl_2=161$ g/L and NaCl=77 g/L, and it was fired at 400° C. for 2 hours. The area ratio of the adsorption-desorption isotherm hysteresis in the gas adsorption method, was 15.3% to the integral value of the adsorption isotherm. Using this catalyst, the evaluation was carried out under the oxygen enriched method conditions, and as a result, the specific activity was 184. Here, the specific activity was evaluated by taking Comparative Example 5 as 100.

Example 17

An oxychlorination catalyst, wherein the Mg/Cu ratio was 0.50, was prepared under the same conditions as in Example 3 except that the composition of the immersion solution was changed to $CuCl_2=161$ g/L and $MgCl_2.2H_2O=267$ g/L, and it was fired at 400° C. for 2 hours. The area ratio of the adsorption-desorption isotherm hysteresis in the gas adsorption method was 14.8% to the integral value of the adsorption isotherm. Using this catalyst, the evaluation was carried out under the oxygen enriched method conditions, and as a result, the specific activity was 254. Here, the specific activity was evaluated by taking Comparative Example 5 as 100.

Example 18

An oxychlorination catalyst wherein the (Na+Mg)/Cu ratio was 0.50, was prepared under the same conditions as in Example 3 except that the composition of the immersion solution was changed to $CuCl_2=161$ g/L, NaCl=26 g/L and $MgCl_2.2H_2O=180$ g/L, and it was fired at 400° C. for 2 hours. The area ratio of the adsorption-desorption isotherm hysteresis in the gas adsorption method was 14.8% to the integral value of the adsorption isotherm. Using this catalyst, the evaluation was carried out under the oxygen enriched method conditions, and as a result, the specific activity was 194. Here, the specific activity was evaluated by taking Comparative Example 5 as 100.

Comparative Example 5

An oxychlorination catalyst wherein the K/Cu ratio was 0.50, was prepared under the same conditions as in Comparative Example 2 except that it was immersed in an immersion solution having a liquid composition of $CuCl_2=240$ g/L and KCl=105 g/L for one hour, and it was fired at 420° C. for 6 hours. The area ratio of the adsorption-desorption isotherm hysteresis in the gas adsorption method was 23.6% to the integral value of the adsorption isotherm. Using this catalyst, the evaluation was carried out under the oxygen enriched method conditions, and as a result, the specific activity was 100. Here, the specific activity was evaluated by taking Comparative Example 5 as 100.

Comparative Example 6

An oxychlorination catalyst wherein the Cs/Cu ratio was 0.50, was prepared under the same conditions as in Comparative Example 2 except that it was immersed in an immersion solution having a liquid composition of $CuCl_2$=240 g/L and CsCl=238 g/L for one hour, and it was fired at 420° C. for 6 hours. The area ratio of the adsorption-desorption isotherm hysteresis in the gas adsorption method was 23.8% to the integral value of the adsorption isotherm. Using this catalyst, the evaluation was carried out under the oxygen enriched method conditions, and as a result, the specific activity was 98. Here, the specific activity was evaluated by taking Comparative Example 5 as 100.

Comparative Example 7

An oxychlorination catalyst wherein the Na/Cu ratio was 0.50, was prepared under the same conditions as in Comparative Example 2 except that it was immersed in an immersion solution having a liquid composition of $CuCl_2$=255 g/L and NaCl=91 g/L for 30 minutes. The area ratio of the adsorption-desorption isotherm hysteresis in the gas adsorption method was 23.8% to the integral value of the adsorption isotherm. Using this catalyst, the evaluation was carried out under the oxygen enriched method conditions, and as a result, the specific activity was 148. Here, the specific activity was evaluated by taking Comparative Example 5 as 100.

Comparative Example 8

An oxychlorination catalyst wherein the Mg/Cu ratio was 0.50, was prepared under the same conditions as in Comparative Example 2 except that it was immersed in an immersion solution having a liquid composition of CuCl2=255 g/L and MgCl2.2H2O=293 g/L for 30 minutes, and it was fired at 250° C. for 4 hours. The area ratio of the adsorption-desorption isotherm hysteresis in the gas adsorption method was 23.7% to the integral value of the adsorption isotherm. Using this catalyst, the evaluation was carried out under the oxygen enriched method conditions, and as a result, the specific activity was 217. Here, the specific activity was evaluated by taking Comparative Example 5 as 100.

Comparative Example 9

An oxychlorination catalyst wherein the (Na+Mg)/Cu ratio was 0.50, was prepared under the same conditions as Example 2 except that it was immersed in an immersion solution having a liquid composition of $CuCl_2$=255 g/L, NaCl=32 g/L and $MgCl_2.2H_2O$=220 g/L for 30 minutes, and it was fired at 250° C. for 4 hours. The area ratio of the adsorption-desorption isotherm hysteresis in the gas adsorption method was 23.9% to the integral value of the adsorption isotherm. Using this catalyst, the evaluation was carried out under the oxygen enriched method conditions, and as a result, the specific activity was 166. Here, the specific activity was evaluated by taking Comparative Example 5 as 100.

TABLE 2

Evaluation results under oxygen enriched method conditions

| | | Example | | | | | Example | | |
| --- | --- | --- | --- | --- | --- | --- | --- | --- | --- |
| | | 9 | 10 | 11 | 12 | 13 | 14 | 15 | 16 |
| Shape | | Hollow cylindrical | | | | | Hollow cylindrical | | |
| Hysteresis ratio (%) | | 13.2 | 13.5 | 13.3 | 13.1 | 13.4 | 15.0 | 15.1 | 15.3 |
| Supported amount (wt %) | $CuCl_2$ | 11.2 | 11.8 | 12.1 | 11.6 | 12.2 | 12.4 | 10.9 | 12.3 |
| | KCl | 3.1 | — | — | — | — | 3.4 | — | — |
| | CsCl | — | 7.4 | — | — | — | — | 6.8 | — |
| | NaCl | — | — | 2.6 | — | 1.1 | — | — | 2.7 |
| | $MgCl_2$ | — | — | — | 4.1 | 2.5 | — | — | — |
| Alkali/Cu (mol/mol) | | 0.50 | 0.50 | 0.50 | 0.50 | 0.50 | 0.50 | 0.50 | 0.50 |
| Ethylene conversion (mmol/(Cat · cc · h)) | | 1.3 | 1.3 | 1.9 | 2.8 | 2.2 | 1.3 | 1.3 | 2.0 |
| Specific activity | | 119 | 118 | 177 | 260 | 198 | 117 | 115 | 184 |

| | | Example | | Comparative Example | | | | |
| --- | --- | --- | --- | --- | --- | --- | --- | --- |
| | | 17 | 18 | 5 | 6 | 7 | 8 | 9 |
| Shape | | Hollow cylindrical | | Hollow cylindrical | | | | |
| Hysteresis ratio (%) | | 14.8 | 14.8 | 23.6 | 23.8 | 23.8 | 23.7 | 23.9 |
| Supported amount (wt %) | $CuCl_2$ | 11.0 | 11.9 | 10.8 | 11.3 | 11.5 | 12.0 | 11.7 |
| | KCl | — | — | 3.0 | — | — | — | — |
| | CsCl | — | — | — | 7.1 | — | — | — |
| | NaCl | — | 1.0 | — | — | 2.5 | — | 1.0 |
| | $MgCl_2$ | 3.9 | 2.6 | — | — | — | 4.3 | 2.5 |
| Alkali/Cu (mol/mol) | | 0.50 | 0.50 | 0.50 | 0.50 | 0.50 | 0.50 | 0.50 |

TABLE 2-continued

Evaluation results under oxygen enriched method conditions

| Ethylene conversion (mmol/(Cat · cc · h)) | 2.8 | 2.1 | 1.1 | 1.1 | 1.6 | 2.4 | 1.8 |
|---|---|---|---|---|---|---|---|
| Specific activity | 254 | 194 | 100 | 98 | 148 | 217 | 166 |

*Specific activity standard: Comparative Example 5

Example 19

Using the catalyst prepared in Example 9, the evaluation was carried out under the oxygen method conditions, and as a result, the specific activity was 374. Here, the specific activity was evaluated by taking Comparative Example 10 as 100.

Example 20

Using the catalyst prepared in Example 10, the evaluation was carried out under the oxygen method conditions, and as a result, the specific activity was 364. Here, the specific activity was evaluated by taking Comparative Example 10 as 100.

Example 21

Using the catalyst prepared in Example 11, the evaluation was carried out under the oxygen method conditions, and as a result, the specific activity was 340. Here, the specific activity was evaluated by taking Comparative Example 10 as 100.

Example 22

Using the catalyst prepared in Example 12, the evaluation was carried out under the oxygen method conditions, and as a result, the specific activity was 259. Here, the specific activity was evaluated by taking Comparative Example 10 as 100.

Example 23

Using the catalyst prepared in Example 13, the evaluation was carried out under the oxygen method conditions, and as a result, the specific activity was 312. Here, the specific activity was evaluated by taking Comparative Example 10 as 100.

Example 24

Using the catalyst prepared in Example 14, the evaluation was carried out under the oxygen method conditions, and as a result, the specific activity was 202. Here, the specific activity was evaluated by taking Comparative Example 10 as 100.

Example 25

Using the catalyst prepared in Example 15, the evaluation was carried out under the oxygen method conditions, and as a result, the specific activity was 197. Here, the specific activity was evaluated by taking Comparative Example 10 as 100.

Example 26

Using the catalyst prepared in Example 16, the evaluation was carried out under the oxygen method conditions, and as a result, the specific activity was 184. Here, the specific activity was evaluated by taking Comparative Example 10 as 100.

Example 27

Using the catalyst prepared in Example 17, the evaluation was carried out under the oxygen method conditions, and as a result, the specific activity was 144. Here, the specific activity was evaluated by taking Comparative Example 10 as 100.

Example 28

Using the catalyst prepared in Example 18, the evaluation was carried out under the oxygen method conditions, and as a result, the specific activity was 168. Here, the specific activity was evaluated by taking Comparative Example 10 as 100.

Comparative Example 10

Using the catalyst prepared in Comparative Example 5, the evaluation was carried out under the oxygen method conditions, and as a result, the specific activity was 100. Here, the specific activity was evaluated by taking Comparative Example 10 as 100.

Comparative Example 11

Using the catalyst prepared in Comparative Example 6, the evaluation was carried out under the oxygen method conditions, and as a result, the specific activity was 98. Here, the specific activity was evaluated by taking Comparative Example 10 as 100.

Comparative Example 12

Using the catalyst prepared in Comparative Example 7, the evaluation was carried out under the oxygen method conditions, and as a result, the specific activity was 91. Here, the specific activity was evaluated by taking Comparative Example 10 as 100.

Comparative Example 13

Using the catalyst prepared in Comparative Example 8, the evaluation was carried out under the oxygen method conditions, and as a result, the specific activity was 71. Here, the specific activity was evaluated by taking Comparative Example 10 as 100.

Comparative Example 14

Using the catalyst prepared in Comparative Example 9, the evaluation was carried out under the oxygen method conditions, and as a result, the specific activity was 76. Here, the specific activity was evaluated by taking Comparative Example 10 as 100.

TABLE 3

Evaluation results under oxygen method conditions

| | | Example | | | | | Example | | |
|---|---|---|---|---|---|---|---|---|---|
| | | 19 | 20 | 21 | 22 | 23 | 24 | 25 | 26 |
| Shape | | Hollow cylindrical | | | | | Hollow cylindrical | | |
| Hysteresis ratio (%) | | 13.2 | 13.5 | 13.3 | 13.1 | 13.4 | 15.0 | 15.1 | 15.3 |
| Supported amount (wt %) | $CuCl_2$ | 11.2 | 11.8 | 12.1 | 11.6 | 12.2 | 12.4 | 10.9 | 12.3 |
| | KCl | 3.1 | — | — | — | — | 3.4 | — | — |
| | CsCl | — | 7.4 | — | — | — | — | 6.8 | — |
| | NaCl | — | — | 2.6 | — | 1.1 | — | — | 2.7 |
| | $MgCl_2$ | — | — | — | 4.1 | 2.5 | — | — | — |
| Alkali/Cu (mol/mol) | | 0.50 | 0.50 | 0.50 | 0.50 | 0.50 | 0.50 | 0.50 | 0.50 |
| Ethylene conversion (mmol/(Cat · cc · h)) | | 5.9 | 5.8 | 5.4 | 4.1 | 4.9 | 3.2 | 3.1 | 2.9 |
| Specific activity | | 374 | 364 | 340 | 259 | 312 | 202 | 197 | 184 |

| | | Example | | Comparative Example | | | | |
|---|---|---|---|---|---|---|---|---|
| | | 27 | 28 | 10 | 11 | 12 | 13 | 14 |
| Shape | | Hollow cylindrical | | Hollow cylindrical | | | | |
| Hysteresis ratio (%) | | 14.8 | 14.8 | 23.6 | 23.8 | 23.8 | 23.7 | 23.9 |
| Supported amount (wt %) | $CuCl_2$ | 11.0 | 11.9 | 10.8 | 11.3 | 11.5 | 12.0 | 11.7 |
| | KCl | — | — | 3.0 | — | — | — | — |
| | CsCl | — | — | — | 7.1 | — | — | — |
| | NaCl | — | 1.0 | — | — | 2.5 | — | 1.0 |
| | $MgCl_2$ | 3.9 | 2.6 | — | — | — | 4.3 | 2.5 |
| Alkali/Cu (mol/mol) | | 0.50 | 0.50 | 0.50 | 0.50 | 0.50 | 0.50 | 0.50 |
| Ethylene conversion (mmol/(Cat · cc · h)) | | 2.3 | 2.7 | 1.6 | 1.5 | 1.4 | 1.1 | 1.2 |
| Specific activity | | 144 | 168 | 100 | 98 | 91 | 71 | 76 |

*Specific activity standard: Comparative Example 10

Example 29

50 g of a hollow cylindrical alumina carrier (trade name N611N3, outer diameter: 4.9 mm, inner diameter: 1.8 mm, length: 3.9 mm) manufactured by JGC C&C., was immersed in 100 ml of 1N hydrochloric acid for 2 hours, followed by draining, drying at 120° C. and firing at 500° C. for 5 hours in the air, to obtain a hollow cylindrical alumina carrier wherein the area ratio of the adsorption-desorption isotherm hysteresis in the gas adsorption method was 12.5% to the integral value of the adsorption isotherm. To 30 g of this alumina carrier, water was sufficiently absorbed, and then, it was immersed in 80 mL of an aqueous solution of $CuCl_2$=174 g/L and KCl=136 g/L for 4 hours. The alumina carrier was taken out from the immersion solution and dried at 120° C. for 2 hours using a muffle furnace. It was then fired at 250° C. for 4 hours, to prepare an oxychlorination catalyst wherein the K/Cu ratio was 0.80. The area ratio of the adsorption-desorption isotherm hysteresis in the gas adsorption method, was 13.6% to the integral value of the adsorption isotherm. As a result of the quantitative analysis, it was an alumina catalyst containing 12.9% of $CuCl_2$ and 5.7% of KCl. This catalyst and a spherical alumina-silica diluent having a diameter of 5.0 mm and a specific surface area of 0.1 $m^2$/g were mixed, and evaluated in accordance with the reaction method under the air method conditions.

Example 30

The evaluation was carried out by the same method as in Example 29 except that as the diluent, a cylindrical graphite diluent having a diameter of 5.0 mm, a length of the side surface of 5.0 mm and a specific surface area of 1.7 $m^2$/g, was used.

Example 31

The evaluation was carried out by the same method as in Example 29 except that as the diluent, a hollow cylindrical alumina-silica diluent having an outer diameter of the hollow cylinder of 6.4 mm, an inner diameter of 3.5 mm, a length of the side surface of 5.0 mm and a specific surface area of 0.094 $m^2$/g, was used.

Example 32

The evaluation was carried out by the same method as in Example 29 except that as the diluent, a hollow cylindrical alumina-silica diluent having an outer diameter of the hollow cylinder of 6.4 mm, an inner diameter of 3.5 mm, a length of the side surface of 6.4 mm and a specific surface area of 0.094 $m^2$/g, was used.

Example 33

The evaluation was carried out by the same method as in Example 29 except that as the diluent, a hollow cylindrical alumina-silica diluent having an outer diameter of the hollow cylinder of 5.0 mm, an inner diameter of 2.5 mm, a length of the side surface of 5.0 mm and a specific surface area of 0.094 $m^2$/g, was used.

Example 34

The evaluation was carried out by the same method as in Example 29 except that as the diluent, a hollow cylindrical graphite diluent having an outer diameter of the hollow cylinder of 5.0 mm, an inner diameter of 2.0 mm, a length of the side surface of 5.0 mm and a specific surface area of 1.7 m²/g, was used.

Example 35

The evaluation was carried out by the same method as in Example 29 except that as the diluent, a hollow cylindrical graphite diluent having an outer diameter of the hollow cylinder of 6.0 mm, an inner diameter of 2.5 mm, a length of the side surface of 5.0 mm and a specific surface area of 1.7 m²/g, was used.

Comparative Example 15

The evaluation was carried out by the same method as in Example 29 except that as the diluent, an irregular shape graphite diluent having a diameter of 5.0 mm, a length of the side surface of from 1.0 to 8.0 mm and a specific surface area of 1.7 m²/g, was used.

Comparative Example 16

50 g of a hollow cylindrical alumina carrier (trade name N611N3, outer diameter: 4.9 mm, inner diameter: 1.8 mm, length: 3.9 mm) manufactured by JGC C&C., was immersed in pure water for 1 hour, followed by draining, drying at 120° C. and firing at 700° C. for 5 hours in the air, to obtain a hollow cylindrical alumina carrier wherein the area ratio of the adsorption-desorption isotherm hysteresis in the gas adsorption method was 16.2% to the integral value of the adsorption isotherm. To 30 g of this alumina carrier, water was fully absorbed, and then, it was immersed in 80 mL of an aqueous solution of CuCl₂=255 g/L and KCl=140 g/L for two hours. The alumina carrier was taken out from the immersion solution and dried at 120° C. for 2 hours using a muffle furnace. Then, it was fired at 420° C. for 6 hours, to prepare an oxychlorination catalyst wherein the K/Cu ratio was 0.80. The area ratio of the adsorption-desorption isotherm hysteresis in the gas adsorption method, was 24.5% to the integral value of the adsorption isotherm. As a result of the quantitative analysis, it was an alumina catalyst containing 12.7% of CuCl₂ and 5.6% of KCl. The evaluation was carried out by the same method as in Example 29 except that 15 ml of this catalyst and 15 ml a hollow cylindrical graphite diluent having an outer diameter of 5.0 mm, an inner diameter of 2.0 mm, a length of the side surface of 5.0 mm and a specific surface area of 1.7 m²/g, were mixed.

TABLE 4

Evaluation results of diluent

|  |  | Ex. 29 | Ex. 30 | Ex. 31 | Ex. 32 | Ex. 33 | Ex. 34 | Ex. 35 | Comp. Ex. 15 | Comp. Ex. 16 |
|---|---|---|---|---|---|---|---|---|---|---|
| Oxychlorination catalyst | Shape | | | | Hollow cylindrical | | | | | |
| | Hysteresis ratio (%) | | | | 13.6 | | | | | 24.5 |
| | Supported amount CuCl₂ KCl (wt %) | | | | 12.9 5.7 | | | | | 12.7 5.6 |
| | K/Cu ratio (mol/mol) | | | | 0.80 | | | | | 0.80 |
| Diluent | Material | Alumina-silica | Graphite | Alumina-silica | Alumina-silica | Alumina-silica | Graphite | Graphite | Graphite | Graphite |
| | Shape | Spherical | Cylindrical | Hollow cylindrical | Hollow cylindrical | Hollow cylindrical | Hollow cylindrical | Hollow cylindrical | Irregular | Hollow cylindrical |
| | Outer diameter or diameter (mm) | 5.0 | 5.0 | 6.4 | 6.4 | 5.0 | 5.0 | 6.0 | 5.0 | 5.0 |
| | Inner diameter (mm) | — | — | 3.5 | 3.5 | 2.5 | 2.0 | 2.5 | — | 2.0 |
| | Length (mm) | — | 5.0 | 5.0 | 6.4 | 5.0 | 5.0 | 5.0 | 1.0 to 8.0 | 5.0 |
| Reaction results | Specific activity | | | | 159 | | | | | 100 |
| | EDC selectivity (%) | 99.3 | 99.4 | 99.4 | 99.3 | 99.4 | 99.6 | 99.6 | 99.1 | 98.7 |
| | Top temperature (° C.) | 243.4 | 240.8 | 241.6 | 242.9 | 240.7 | 237.8 | 238.4 | 243.8 | 238.3 |
| Pressure loss (hPa) | 400 mm | 5.1 | 7.3 | 4.2 | 3.9 | 5.4 | 6.0 | 5.2 | 8.0 | 6.5 |
| | 800 mm | 10.1 | 11.7 | 5.8 | 5.1 | 8.1 | 9.5 | 7.8 | 13.3 | 10.0 |
| | 1,200 mm | 14.6 | 15.8 | 7.4 | 6.4 | 10.7 | 12.7 | 10.3 | 18.7 | 13.2 |

The present invention has been described in detail also with reference to specific embodiments. However, it is apparent for those skilled in the art that it is possible to make various changes and modifications without departing from the spirit and scope of the invention.

The entire disclosures of Japanese Patent Application No. 2013-148891 filed on Jul. 17, 2013 and Japanese Patent Application No. 2014-032919 filed on Feb. 24, 2014 including specifications, claims, drawings and summaries are incorporated herein by reference in their entireties.

INDUSTRIAL APPLICABILITY

The heterogeneous catalyst of the invention can be used particularly as a catalyst for producing 1,2-dichloroethane useful as a raw material for a vinyl chloride monomer, from ethylene, and at that time, the ethylene conversion rate and the 1,2-dichloroethane selectivity become very high such being excellent also economically. Further, stable production is thereby possible, and thus, it is excellent in safety.

REFERENCE SYMBOLS

1: hysteresis, 2: desorption side, 3: adsorption side

The invention claimed is:

1. A catalyst which is a heterogeneous catalyst having a metal compound supported on a porous carrier and which is characterized in that the integral value of the hysteresis occurring between an adsorption isotherm and a desorption isotherm by a gas adsorption method, is at most 19% to the total integral value of the adsorption isotherm, wherein the heterogeneous catalyst has a hollow cylindrical shape, and wherein the metal in the metal compound is a metal in Group 1, Group 2 or Group 11 in the Periodic Table.

2. The catalyst according to claim 1, wherein the porous carrier is alumina, silica, silica-alumina, zeolite, titanium oxide, zirconium oxide or magnesium oxide.

3. The catalyst according to claim 1, wherein the metal compound is an oxide or halide.

4. The catalyst according to claim 1, wherein the metal compound is copper chloride.

5. The catalyst according to claim 1, wherein the metal compound is copper chloride, and at least one metal chloride selected from the group consisting of potassium chloride, cesium chloride, sodium chloride and magnesium chloride.

6. The catalyst according to claim 4, wherein the amount of copper chloride supported, is from 3 to 25 wt %.

7. The catalyst according to claim 5, wherein the amount of the metal chloride supported, is from 0.1 to 20 wt %.

8. The catalyst according to claim 1, wherein the gas adsorption method is a nitrogen adsorption method.

9. The catalyst according to claim 1, wherein the hollow cylindrical shape has an outer diameter of from 3 to 6 mm, an inner diameter of from 1 to less than 3 mm and a length of from 3 to 6 mm.

10. The catalyst according to claim 1, wherein the catalyst is used in an application for oxychlorination of ethylene.

11. A method for producing 1,2-dichloroethane, which comprises carrying out oxychlorination of ethylene, hydrogen chloride and oxygen in the presence of the catalyst as defined in claim 1.

12. A catalyst system for producing 1,2-dichloroethane from ethylene, hydrogen chloride and oxygen, which comprises the catalyst as defined in claim 1, and a diluent having a spherical shape, cylindrical shape or hollow cylindrical shape.

13. The catalyst system for producing 1,2-dichloroethane according to claim 12, wherein the diluent is at least one member selected from the group consisting of, alumina, silica, alumina-silica, silicon carbide, aluminum nitride, carbon and graphite.

14. The catalyst system for producing 1,2-dichloroethane according to claim 12, wherein the outer diameter D of the diluent having a spherical shape is a dimension (mm) of the following formula:

$$4.5 \leq D \leq 7.0.$$

15. The catalyst system for producing 1,2-dichloroethane according to claim 12, wherein the outer diameter $De^1$ of the cylinder of the diluent having a cylindrical shape is a dimension (mm) of the following formula, and the length $L^1$ of the side surface thereof is a dimension (mm) of the following formula:

$$4.5 \leq De^1 \leq 7.0$$

$$4.0 \leq L^1 \leq 7.0.$$

16. The catalyst system for producing 1,2-dichloroethane according to claim 12, wherein the outer diameter $De^2$ of the hollow cylinder of the diluent having a hollow cylindrical shape is a dimension (mm) of the following formula, the inner diameter Di thereof is a dimension (mm) of the following formula, the length $L^2$ of the side surface thereof is a dimension (mm) of the following formula, and the relation between the outer diameter $De^2$ and the inner diameter Di is represented by the formula:

$$4.5 \leq De^2 \leq 7.0$$

$$1.5 \leq Di \leq 4.0$$

$$4.0 \leq L^2 \leq 7.0$$

$$De^2/3 \leq Di.$$

17. The catalyst system for producing 1,2-dichloroethane according to claim 12, wherein the outer diameter of the diluent is a length equal to the length of the oxychlorination catalyst.

18. A method for producing 1,2-dichloroethane, which is characterized by reacting ethylene, hydrogen chloride and oxygen in the presence of the catalyst system for producing 1,2-dichloroethane as defined in claim 12.

* * * * *